US012597481B2

(12) United States Patent
Yamamoto et al.

(10) Patent No.: US 12,597,481 B2
(45) Date of Patent: Apr. 7, 2026

(54) SYSTEM, MOBILE TERMINAL DEVICE, PROGRAM, AND METHOD

(71) Applicants: CarbGeM Inc., Tokyo (JP); NATIONAL CENTER FOR GLOBAL HEALTH AND MEDICINE, Tokyo (JP)

(72) Inventors: Kei Yamamoto, Tokyo (JP); Isao Miyatsuka, Tokyo (JP); My An Le, Tokyo (JP)

(73) Assignees: CARBGEM INC., Tokyo (JP); NATIONAL CENTER FOR GLOBAL HEALTH AND MEDICINE, Tokyo (JP)

( * ) Notice: Subject to any disclaimer, the term of this patent is extended or adjusted under 35 U.S.C. 154(b) by 294 days.

(21) Appl. No.: 18/284,414

(22) PCT Filed: Oct. 1, 2021

(86) PCT No.: PCT/JP2021/036497
§ 371 (c)(1),
(2) Date: Sep. 27, 2023

(87) PCT Pub. No.: WO2022/208948
PCT Pub. Date: Oct. 6, 2022

(65) Prior Publication Data
US 2024/0071562 A1     Feb. 29, 2024

(30) Foreign Application Priority Data
Apr. 2, 2021     (JP) ................................. 2021-063270

(51) Int. Cl.
| | | |
|---|---|---|
| *G06K 9/00* | (2022.01) | |
| *G06V 10/94* | (2022.01) | |

(Continued)

(52) U.S. Cl.
CPC ........... *G16B 15/00* (2019.02); *G06V 10/945* (2022.01); *G06V 20/693* (2022.01); *G06V 20/698* (2022.01); *G06V 2201/03* (2022.01)

(58) Field of Classification Search
None
See application file for complete search history.

(56) References Cited

U.S. PATENT DOCUMENTS

| | | |
|---|---|---|
| 2013/0325502 A1 | 12/2013 | Robicsek et al. |
| 2019/0212349 A1 | 7/2019 | Galiano |

(Continued)

FOREIGN PATENT DOCUMENTS

| | | |
|---|---|---|
| JP | 2005-25281 A | 1/2005 |
| JP | 2016-110376 A | 6/2016 |

(Continued)

OTHER PUBLICATIONS

Matsuki, Yoshihiko et al., "Relation between Approaches Using Antibiogram and Gram Staining to Help Design Antimicrobial Regimens and the Amounts of Antimicrobials Used and Drug Sensitivity of Pseudomonas aeruginosa", Japanese Journal of Infection Prevention and Control., Jun. 5, 2012, vol. 27, No. 2, pp. 105-112, ISSN: 1883-2407, entire text, all drawings, along with an English abstract (provided on last page of document).

(Continued)

*Primary Examiner* — Sj Park
(74) *Attorney, Agent, or Firm* — Greenblum & Bernstein, P.L.C.

(57) ABSTRACT

An example system according to the present invention can provide a more convenient system.
A mobile terminal device includes an acquisition unit configured to acquire information specifying a bacterial strain and information specifying a sensitivity rate, and a specification unit configured to specify, using an antibiogram, (Continued)

information on one or a plurality of antimicrobial agents, each of the antimicrobial agents satisfying the sensitivity rate for the bacterial strain. The information on the antimicrobial agent includes a sensitivity rate of the antimicrobial agent, a spectrum score for the antimicrobial agent, and/or an AWaRe classification of the antimicrobial agent. The mobile terminal device includes a display unit configured to display a plurality of sensitivity rate candidates, and the sensitivity rate is selected, by a user, from among the plurality of sensitivity rate candidates.

17 Claims, 11 Drawing Sheets

(51) Int. Cl.
    *G06V 20/69*       (2022.01)
    *G16B 15/00*       (2019.01)

(56)              References Cited

U.S. PATENT DOCUMENTS

| | | | |
|---|---|---|---|
| 2020/0097727 A1* | 3/2020 | Stumpe | G02B 21/361 |
| 2021/0040530 A1* | 2/2021 | Balagurusamy | G06T 7/20 |

FOREIGN PATENT DOCUMENTS

| | | | |
|---|---|---|---|
| JP | 2017-184737 A | | 10/2017 |
| JP | 2019-82789 A | | 5/2019 |
| JP | 2019-521682 A | | 8/2019 |
| JP | 2020187604 A | * | 11/2020 |

OTHER PUBLICATIONS

International Search Report Issued in International Patent Application No. PCT/JP2021/036497, dated Oct. 26, 2021, along with an English translation thereof.

* cited by examiner

FIG. 4

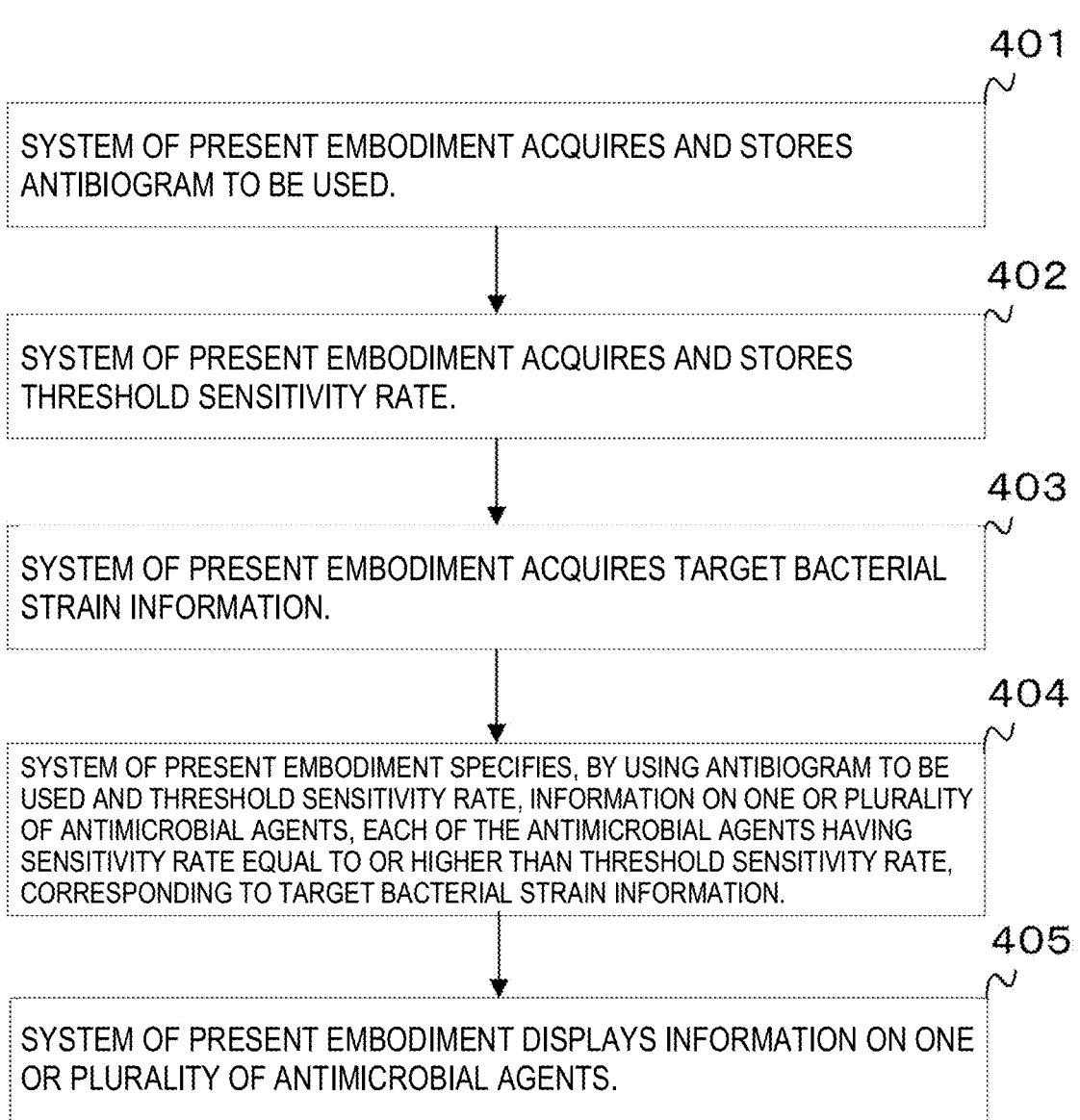

401

SYSTEM OF PRESENT EMBODIMENT ACQUIRES AND STORES ANTIBIOGRAM TO BE USED.

402

SYSTEM OF PRESENT EMBODIMENT ACQUIRES AND STORES THRESHOLD SENSITIVITY RATE.

403

SYSTEM OF PRESENT EMBODIMENT ACQUIRES TARGET BACTERIAL STRAIN INFORMATION.

404

SYSTEM OF PRESENT EMBODIMENT SPECIFIES, BY USING ANTIBIOGRAM TO BE USED AND THRESHOLD SENSITIVITY RATE, INFORMATION ON ONE OR PLURALITY OF ANTIMICROBIAL AGENTS, EACH OF THE ANTIMICROBIAL AGENTS HAVING SENSITIVITY RATE EQUAL TO OR HIGHER THAN THRESHOLD SENSITIVITY RATE, CORRESPONDING TO TARGET BACTERIAL STRAIN INFORMATION.

405

SYSTEM OF PRESENT EMBODIMENT DISPLAYS INFORMATION ON ONE OR PLURALITY OF ANTIMICROBIAL AGENTS.

FIG. 8

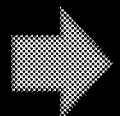

E. COLI

SENSITIVITY RATE AS CRITERION:
90% OR MORE

> RETURN TO SELECTION OF SENSITIVITY RATE

CEFMETAZOLE 99% (*23.5, Watch)
*SCORE OF CEFUROXIME IS SUBSTITUTED

AMIKACIN 99% (35.5 Access) (CAUTION)
(CAUTION) MONOTHERAPY IS NOT RECOMMENDED EXCEPT FOR
URINARY TRACT INFECTION ↓↓ REFER TO OTHER CHEMICAL AGENTS
MEROPENEM 99% (41.5, Watch)
PIPERACILLIN/TAZOBACTAM *98% (42.25, Watch)
*SENSITIVITY OF ESBL-PRODUCING BACTRIA IS ALSO
DETERMINED BASED ON MIC VALUE.

NARROW DOWN BY SPECIMEN > NOT USABLE

FIG. 9

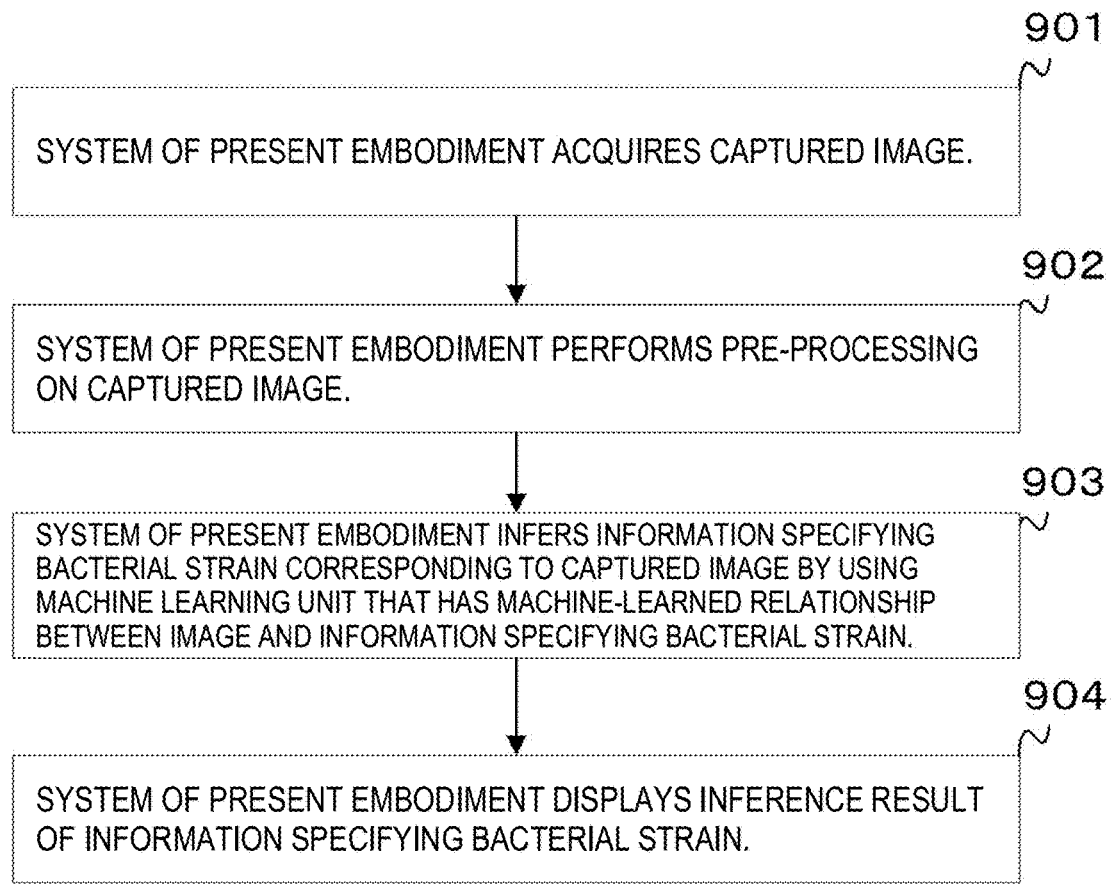

901

SYSTEM OF PRESENT EMBODIMENT ACQUIRES CAPTURED IMAGE.

902

SYSTEM OF PRESENT EMBODIMENT PERFORMS PRE-PROCESSING ON CAPTURED IMAGE.

903

SYSTEM OF PRESENT EMBODIMENT INFERS INFORMATION SPECIFYING BACTERIAL STRAIN CORRESPONDING TO CAPTURED IMAGE BY USING MACHINE LEARNING UNIT THAT HAS MACHINE-LEARNED RELATIONSHIP BETWEEN IMAGE AND INFORMATION SPECIFYING BACTERIAL STRAIN.

904

SYSTEM OF PRESENT EMBODIMENT DISPLAYS INFERENCE RESULT OF INFORMATION SPECIFYING BACTERIAL STRAIN.

FIG. 10

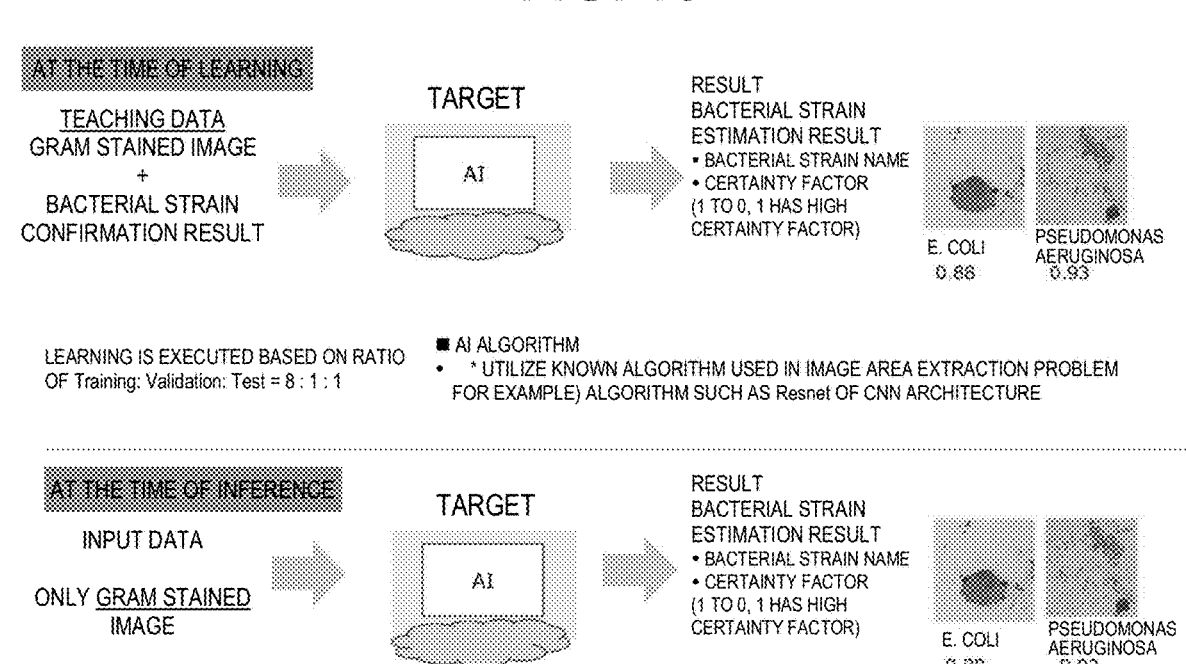

AT THE TIME OF LEARNING

TEACHING DATA
GRAM STAINED IMAGE
+
BACTERIAL STRAIN
CONFIRMATION RESULT

TARGET

AI

RESULT
BACTERIAL STRAIN
ESTIMATION RESULT
• BACTERIAL STRAIN NAME
• CERTAINTY FACTOR
(1 TO 0, 1 HAS HIGH
CERTAINTY FACTOR)

E. COLI
0.86

PSEUDOMONAS
AERUGINOSA
0.93

LEARNING IS EXECUTED BASED ON RATIO
OF Training: Validation: Test = 8 : 1 : 1

■ AI ALGORITHM
•　* UTILIZE KNOWN ALGORITHM USED IN IMAGE AREA EXTRACTION PROBLEM
FOR EXAMPLE) ALGORITHM SUCH AS Resnet OF CNN ARCHITECTURE

AT THE TIME OF INFERENCE

INPUT DATA

ONLY GRAM STAINED
IMAGE

TARGET

AI

RESULT
BACTERIAL STRAIN
ESTIMATION RESULT
• BACTERIAL STRAIN NAME
• CERTAINTY FACTOR
(1 TO 0, 1 HAS HIGH
CERTAINTY FACTOR)

E. COLI
0.88

PSEUDOMONAS
AERUGINOSA
0.93

*FIG. 11*
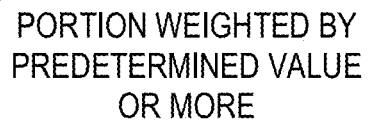
PORTION WEIGHTED BY
PREDETERMINED VALUE
OR MORE
PORTION WEIGHTED BY
VALUE LESS THAN
PREDETERMINED VALUE
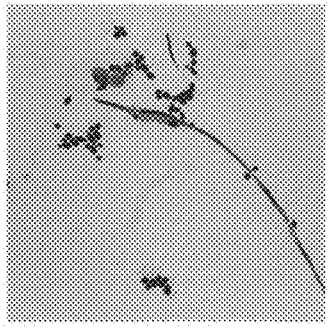
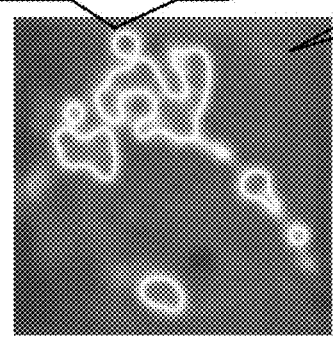
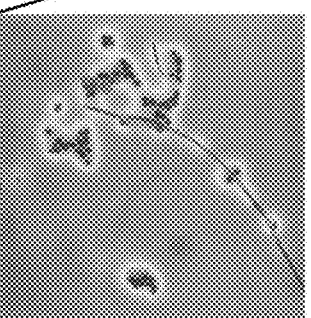
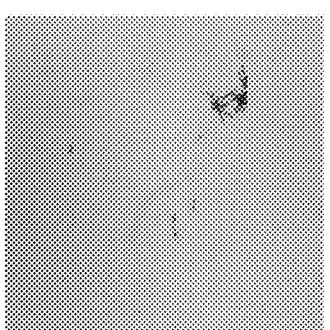
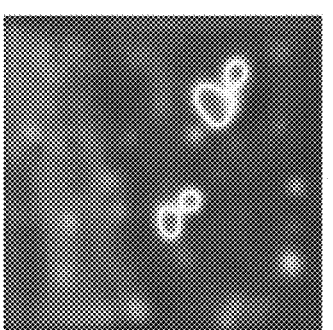
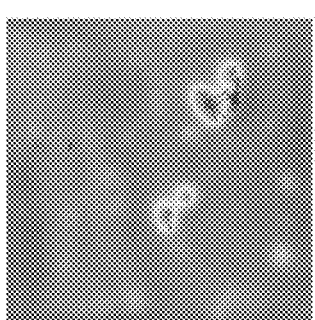

BY USING ATTACHMENT OF OPTICAL MICROSCOPE, ADJUSTMENT IS PERFORMED SO THAT EYEPIECE OF OPTICAL MICROSCOPE AND CAMERA POSITION OF SMARTPHONE ARE ALIGNED, AND OBSERVATION IMAGE OF OPTICAL MICROSCOPE IS IMPORTED INTO SMARTPHONE CAMERA

SYSTEM, MOBILE TERMINAL DEVICE, PROGRAM, AND METHOD

TECHNICAL FIELD

The technology disclosed in the present application relates to a system, a mobile terminal device, a program, and a method.

BACKGROUND ART

In recent years, there has been a demand for improvement in work efficiency for an antibiogram.

CITATION LIST

Patent Literature

Patent Literature 1: JP 2020-187604 A
Patent Literature 2: JP 2019-521682 A
Patent Literature 3: JP 2016-110376 A

SUMMARY OF INVENTION

Technical Problem

However, the technology disclosed in the above-described literature is insufficient in terms of user convenience. Therefore, in order to solve the above-described problems, various embodiments of the present invention provide a system, a mobile terminal device, an information processing apparatus, a program, and/or a method with improved convenience.

Solution to Problem

In one aspect, the present invention provides a mobile terminal device including:
   an acquisition unit configured to acquire information specifying a bacterial strain and information specifying a sensitivity rate; and
   a specification unit configured to specify, using an antibiogram, information on one or a plurality of antimicrobial agents, each of the antimicrobial agents satisfying the sensitivity rate for the bacterial strain.
In another aspect, the present invention provides a method of executing, by a mobile terminal device, the steps of:
   acquiring information specifying a bacterial strain and information specifying a sensitivity rate; and
   specifying, using an antibiogram, information on one or a plurality of antimicrobial agents, each of the antimicrobial agents satisfying the sensitivity rate for the bacterial strain.
In still another aspect, the present invention provides a program configured to cause a mobile terminal device to operate as:
   a unit configured to acquire information specifying a bacterial strain and information specifying a sensitivity rate; and
   a unit configured to specify, using an antibiogram, information on one or a plurality of antimicrobial agents, each of the antimicrobial agents satisfying the sensitivity rate for the bacterial strain.

Advantageous Effects of Invention

According to an embodiment of the present invention, it is possible to provide a system, a mobile terminal device, an information processing apparatus, a program, and/or a method with improved convenience.

BRIEF DESCRIPTION OF DRAWINGS

FIG. 4 is a diagram illustrating a screen display example according to the system of the embodiment.
FIG. 8 is a diagram illustrating a screen display example according to the system of the embodiment.
FIG. 9 is a diagram illustrating a screen display example according to the system of the embodiment.
FIG. 10 is a schematic diagram illustrating one function according to the system of the embodiment.
FIG. 11 is a diagram illustrating a display example according to the system of the embodiment.

DESCRIPTION OF EMBODIMENTS

1. Summary of the Present Invention

Figure 1:
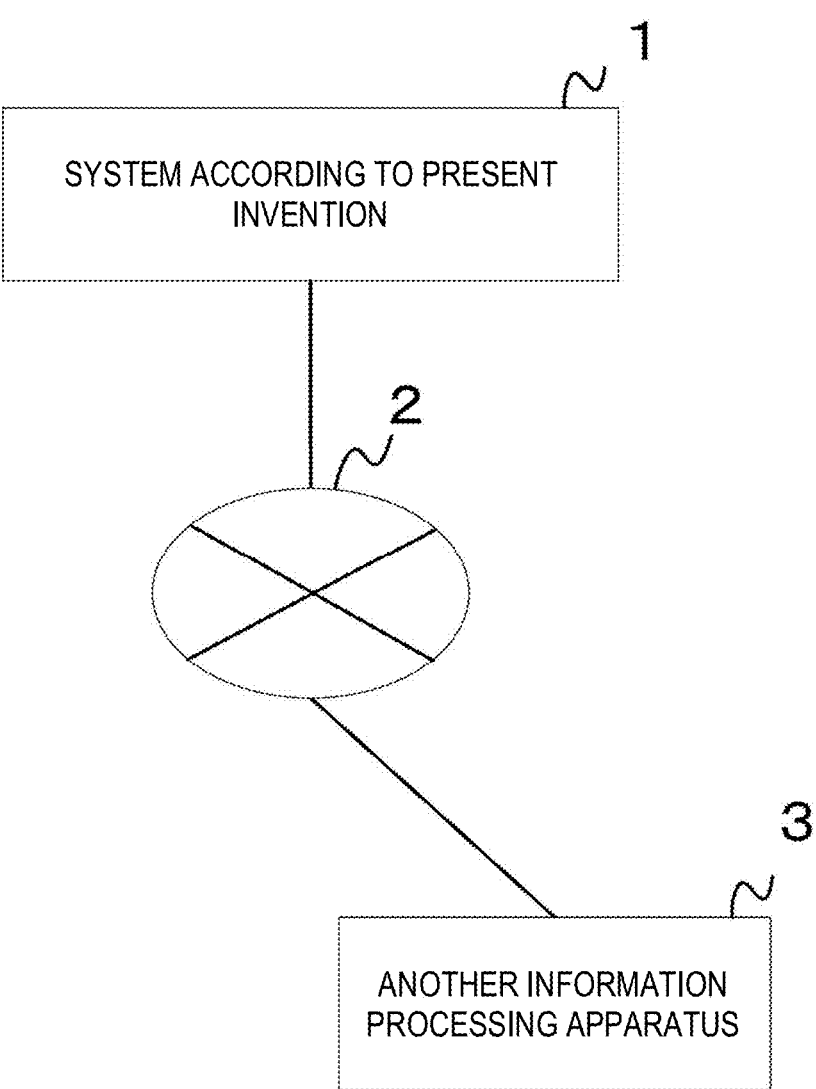
FIG. 1 is a block diagram illustrating a configuration according to a system of an embodiment.
Figure 12:
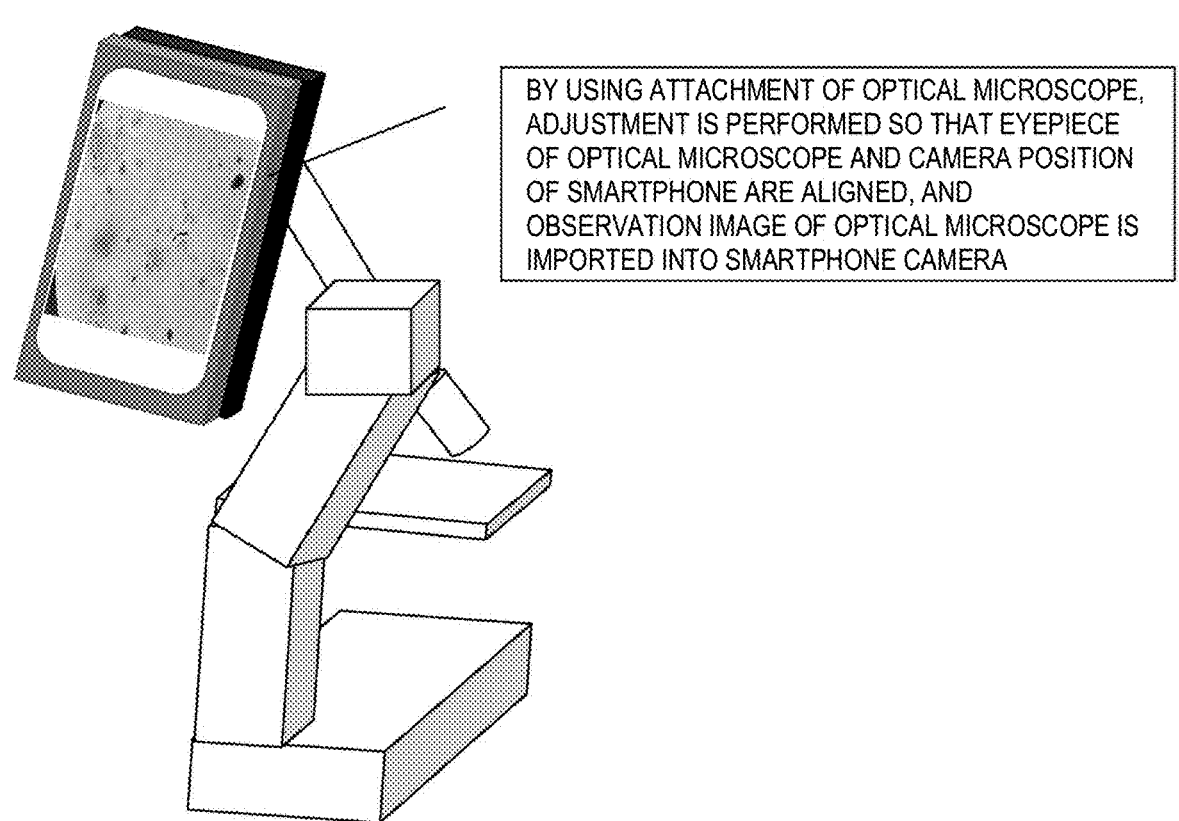
FIG. 12 is a diagram illustrating a usage example of the system according to the embodiment.

A system according to an embodiment of the present invention provides a technology for supporting collection of information on a bacterial strain.
FIG. 1 illustrates an aspect of a system according to an embodiment of the present invention. A function according to the system of the embodiment may be realized by a function only in one mobile terminal device, or may be realized without using a function of another information processing apparatus. In this case, there is an advantage that the user can obtain the benefit of the system according to the present invention only by carrying one mobile terminal device. Particularly, there is an advantage of easily carrying the mobile terminal device to a disaster-stricken area, a medical underpopulated area, and the like. Particularly, when the system according to the present invention is implemented in a smartphone serving as the mobile terminal device, there is an advantage that the system can be easily used because the smartphone is widely used.
Particularly, in a case where the system of the present embodiment is in a mode of using a captured image according to a system of a second embodiment to be described later and includes an imaging device for capturing such a captured image, there is an advantage that information on an antimicrobial agent can be more easily used because the information on the antimicrobial agent can be specified using the captured image captured by such an imaging device.
In addition, in a case where the system of the present embodiment uses a captured image and is implemented in a smartphone having an imaging device, there is an advantage that, for example, a Gram-stained specimen on a preparation can be captured by the smartphone in a state where the specimen can be observed with an optical microscope. In this case, the imaging device according to the system of the present embodiment may be used to capture an image of the Gram-stained specimen on the preparation enlarged at a predetermined magnification. In this case, there is an advantage that the information can be easily collected from the specimen on the preparation and it is not necessary to bring in a large-scale imaging device such as a conventional medical device even at a usage site such as a disaster-stricken area or a medical underpopulated area. Although there are various aspects for realizing such a configuration, for example, FIG. 12 illustrates an aspect in which a smartphone as the system of the present embodiment is detachably fixed to an optical microscope by an attachment of the optical microscope, and an observation image of the optical microscope can be captured by the imaging device of the smartphone.

In addition, in a case where the system according to the present invention is realized by downloadable software via the Internet, there is an advantage that the system can be easily implemented by downloading and installing the software in a mobile terminal device, such as a smartphone or a notebook computer, which can be connected to the Internet and download software.

For example, in the drawing, an information processing apparatus such as a server or a cloud may be accessed via an Internet 2 to download information necessary for the system according to the present invention. As described above, such information may be information downloaded for installing the system according to the present invention, or may be information used when the system according to the present invention is used. The latter may include, for example, the latest antibiogram, an antibiogram related to an area in which the system according to the present invention is used, and the like.

Figure 2:
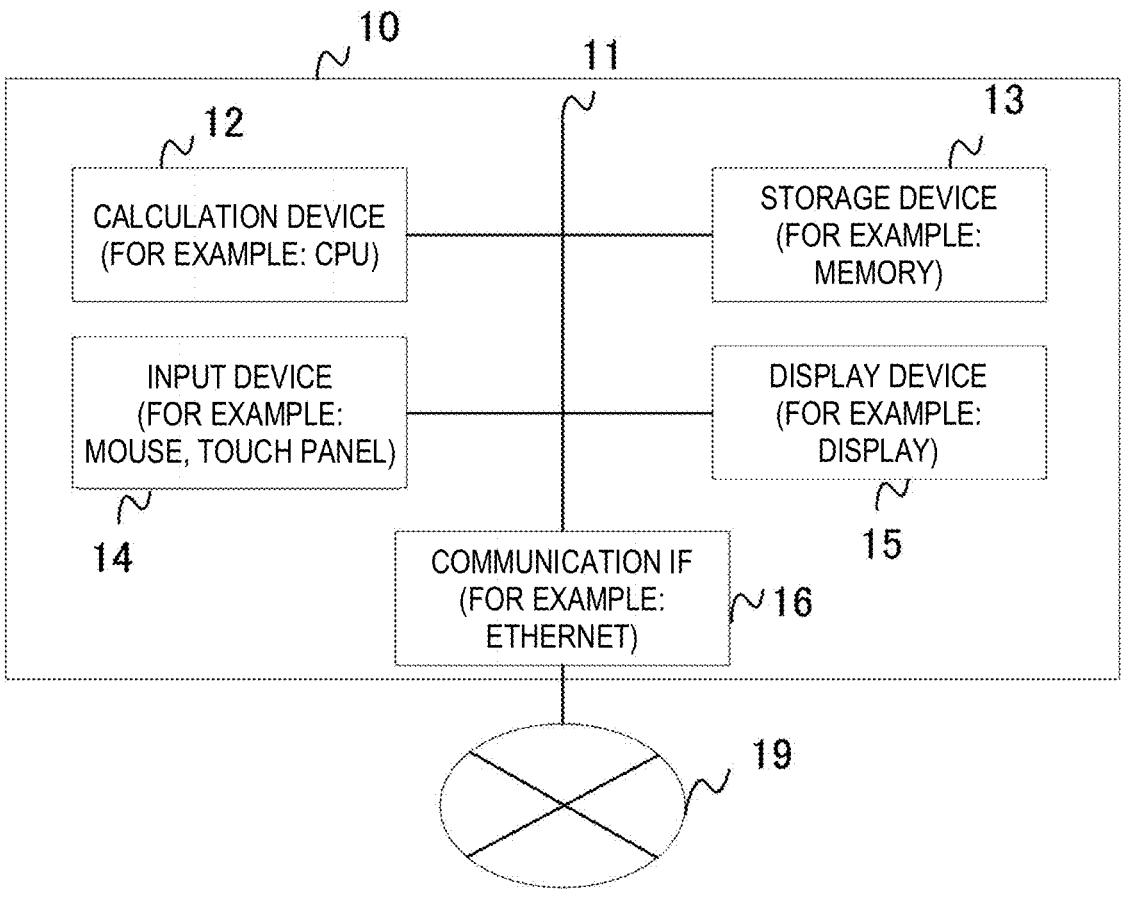
FIG. 2 is a block diagram illustrating a configuration of an information processing apparatus according to the system of the embodiment.
Figure 3:
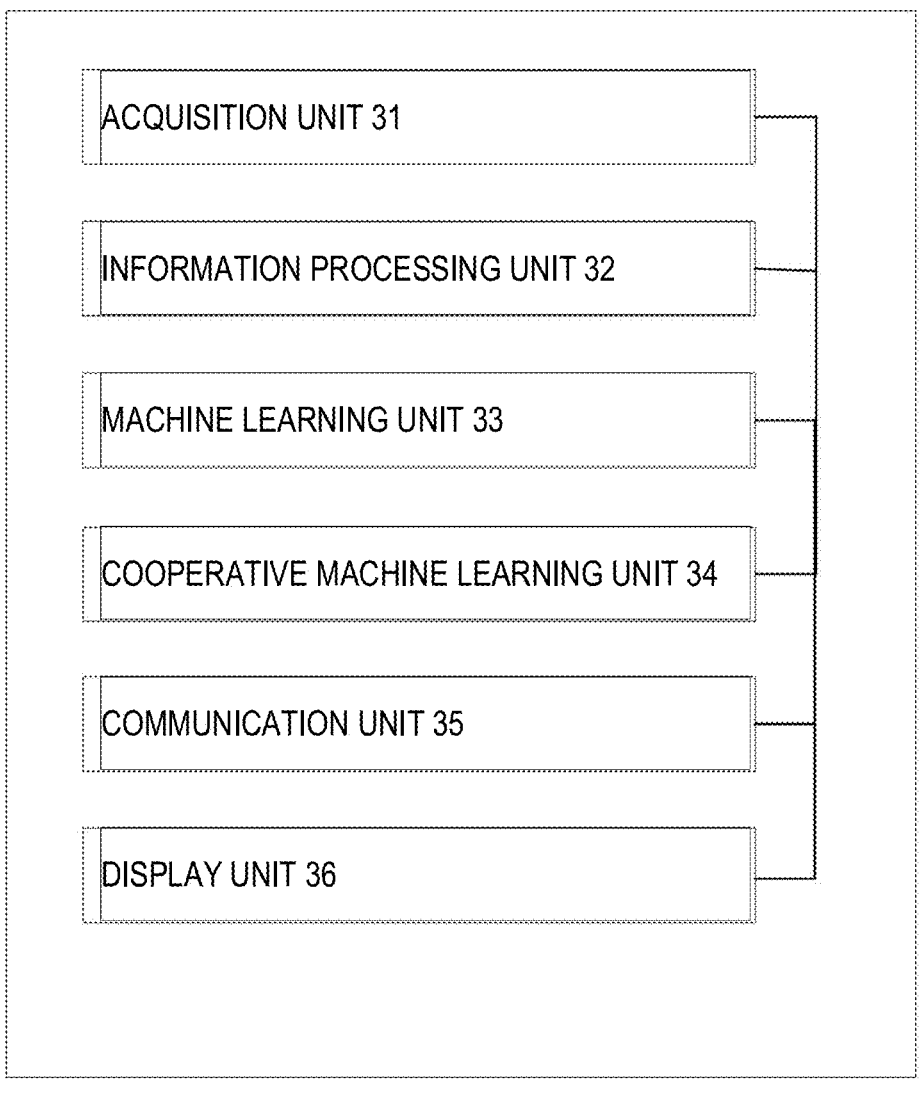
FIG. 3 is a block diagram illustrating a function according to the system of the embodiment.

The system according to the present invention may be an information processing apparatus. FIG. 2 illustrates a configuration of an information processing apparatus 10, and the information processing apparatus 10 can include a bus 11, a calculation unit 12, and a storage unit 13. In addition, an input unit 14, a display unit 15, and a communication IF 16 may be included. The system of the embodiment according to the present invention may include one or a plurality of information processing apparatuses 10.

The bus 11 has a function of transmitting information between the calculation unit 12 and the storage unit 13. The bus 11 may have a function of transmitting information between the input unit 14, the display unit 15, and the communication IF 16.

Examples of the calculation unit 12 include a processor. The processor may be a CPU or an MPU. In short, the calculation unit 12 only needs to have a function capable of executing a command of a program. Furthermore, the calculation unit 12 that implements a function of a machine learning unit may be a processing device capable of processing a machine-learned function. Furthermore, the calculation unit 12 that implements the function of the machine learning unit can process the machine-learned function, but may have a configuration not having a machine learning function. Although a mobile terminal device such as a smartphone has an information processing function lower than that of a server or a cloud, the mobile terminal device does not have a machine learning function and has only a machine-learned function, thereby having an advantage that simple processing can be performed. It is noted that, as one of the methods having only the machine-learned function, the method may be realized by causing software for realizing the machine-learned function to be downloaded and installed in the mobile terminal device.

The storage unit 13 has a function of recording information. The storage unit 13 may be either an external memory or an internal memory, or may be either a main storage device or an auxiliary storage device. It is noted that, in a case where an information processing apparatus is a server or a cloud, the storage unit may be a storage device via a network, a storage device on the cloud, or the like. It is noted that a register, an L1 cache, an L2 cache, and the like that store information at a position close to a calculation device may be included in the calculation unit 12 in a point that the register, the L1 cache, the L2 cache, and the like are not via a bus in the schematic diagram of FIG. 1, but the storage unit 13 may include these elements as a device that records information in the design of the computer architecture. In short, it is sufficient that the calculation unit 12, the storage unit 13, and the bus 11 cooperate to execute information processing. Furthermore, in the above description, the case in which the calculation unit 12 is executed based on the program provided in the storage unit 13 has been described. However, as one of the forms in which the bus 11, the calculation unit 12, and the storage unit 13 are combined, the information processing according to the present system may be realized by a programmable logic device capable of changing a hardware circuit itself or a dedicated circuit in which information processing to be executed is determined.

The input unit 14 has a function of inputting information. Examples of the input unit 14 include pointing devices such as a mouse, a touch panel, and a pen type pointing device. The display unit 15 is, for example, a display. In addition, a liquid crystal display, a plasma display, an organic EL display, or the like may be used. In short, any device that can display information may be used. In addition, a display may include the input unit 14 in a part thereof as in a touch panel.

Hereinafter, examples of various combinations will be described using the above-described information processing apparatus 10. Each example described below is merely an example of a configuration example on the network, and there may be combination examples other than the following combination examples of individual information processing apparatuses in addition to those explicitly illustrated. These combinations may be various combinations based on the common technical knowledge.

2. Function

Some or all of the functions of the invention according to the present application will be described below. The system according to the present invention may include the following acquisition unit, information processing unit, machine learning unit, and/or display unit. For example, a system according to a first embodiment to be described later may include the following acquisition unit, information processing unit, and display unit. In addition, a system according to a second embodiment to be described later may include the following acquisition unit, machine learning unit, cooperative machine learning unit, and display unit. When the system according to the second embodiment to be described later is a mobile terminal device, the following acquisition unit, display unit, and communication unit may be provided. In this case, the mobile terminal device may perform communication such as transmission and reception of information on machine learning with a machine learning unit in the information processing apparatus outside the mobile terminal device. It is noted that the machine learning unit and the cooperative machine learning unit may be provided in a server, a cloud, or the like, and these devices may correspond to the above-described communication.

2.1. Acquisition Unit

The acquisition unit has a function of acquiring information according to the present invention. The acquisition unit may acquire, for example, information according to the present invention, such as a captured image to be described later and/or information specifying a bacterial strain.

The acquisition unit according to the system of the present invention may acquire information according to the present invention from another information processing apparatus, may acquire information according to the present invention based on a user input, or may acquire the information according to the present invention from the system itself according to the present invention.

2.2. Information Processing Unit

The information processing unit has a function of performing information processing. The information processing unit may have a function of performing the information processing mainly using an antibiogram.

2.3. Machine Learning Unit

The machine learning unit has a function of generating an inference result about an image.

The machine learning unit may have machine-learned an image. The machine learning unit may have machine-learned a relationship between an image and appropriateness of the image and/or a relationship between an image and information specifying a bacterial strain in the image.

An artificial intelligence technique may be used in the machine learning unit. For example, the machine learning unit may have machine-learned a relationship between an input and an output, and may generate an output corresponding to an input using such a machine-learned function.

Various methods may be used for the machine learning described above. For example, a neural network using deep learning, a support vector machine, a Bayesian network, clustering, or the like may be used. In addition, the machine learning may be a machine-learned model. Then, the machine-learned model in the document of the present application may be assumed to be used as a program module, which is a part of artificial intelligence software. The learned model of the present invention may be used in a computer including a CPU and a memory. Specifically, the CPU of the computer may operate to perform an operation using a weight in a neural network on input data input to an input layer of the neural network according to an instruction from a learned model stored in the memory, and output a result from an output layer of the neural network.

2.4. Cooperative Machine Learning Unit

The cooperative machine learning unit may have a function of managing a weight in the machine learning unit. Such a weight may be managed using a weight transmitted from the machine learning unit that has completed machine learning. That is, the cooperative machine learning unit may have a function of generating a weight in the cooperative machine learning unit by using a weight transmitted from one or a plurality of machine learning units. The generated weight (in the document of the present application, the weight may be referred to as an "integrated weight") may be transmitted to the machine learning unit.

Figure 13:
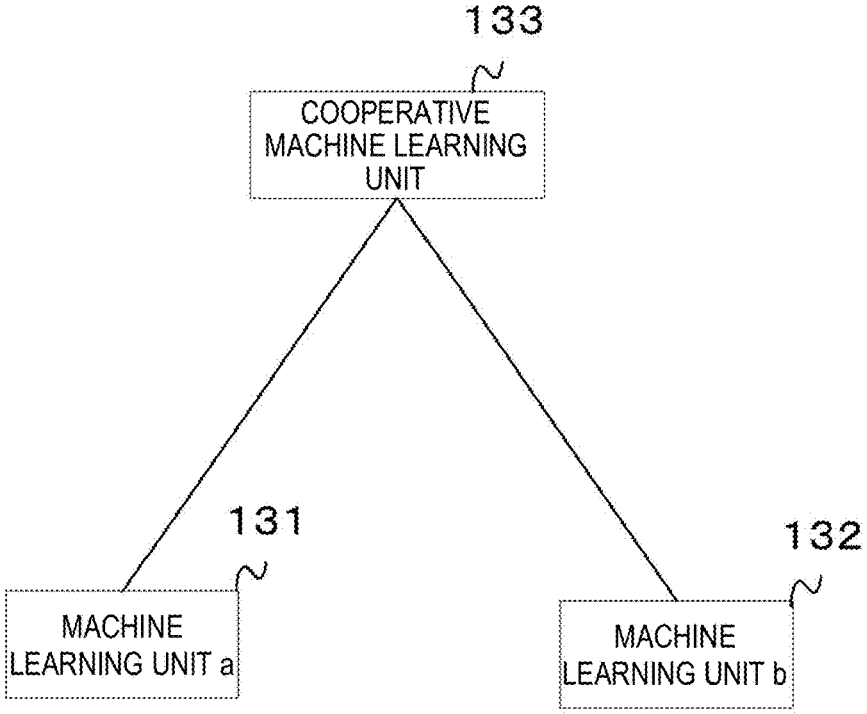
FIG. 13 is a diagram illustrating a configuration function example of the system according to the embodiment.

FIG. 13 is an example illustrating a relationship between the cooperative machine learning unit and the machine learning unit. Each of a machine learning unit a 131 and a machine learning unit b 132 may be connectable to a cooperative machine learning unit 133. Furthermore, the machine learning unit a, the machine learning unit b, and the cooperative machine learning unit may be connectable via a network. Furthermore, the machine learning unit a, the machine learning unit b, and the cooperative machine learning unit may be owned, used, and managed in different medical institutions.

As an example of using such a configuration, the following is considered. First, it is assumed that the machine learning unit a performs machine learning using data A. The data A may be one or a plurality of pieces of data. The machine learning unit a is machine-learned by machine learning, and can generate a weight A corresponding to the machine learning. The machine learning unit a may transmit the weight A to the cooperative machine learning unit. The cooperative machine learning unit may transmit, to the machine learning unit b, the weight A or a product obtained by processing the weight A so as to be applicable to the machine learning unit b. The machine learning unit b may apply the subsequent machine learning function using the weight A or the product obtained by processing the weight A so as to be applicable to the machine learning unit b. In this case, the machine learning unit b has an advantage that it is not necessary to perform learning in the machine learning unit a. That is, the machine learning unit b has an advantage that the function obtained by the machine learning unit a by learning can be obtained by transmission of the weight A or the product obtained by processing the weight A so as to be applicable to the machine learning unit b without using the data used in the learning in the machine learning unit a. This is advantageous in that, in a case where the data used by the machine learning unit a for machine learning includes personal information such as medical information, the machine learning unit b can perform machine learning without transmission of the personal information from the machine learning unit a to the cooperative machine learning unit.

The machine learning unit b may further perform machine learning in the machine learning unit b. The machine learning unit b is machine-learned by machine learning, and can generate a weight B corresponding to the machine learning. The machine learning unit b may transmit the weight B to the cooperative machine learning unit. The cooperative machine learning unit may transmit, to the machine learning unit a, the weight B or a product obtained by processing the weight B so as to be applicable to the machine learning unit a. The machine learning unit a may apply the subsequent machine learning function using the weight B or the product obtained by processing the weight B so as to be applicable to the machine learning unit a. In this case, the machine learning unit a has an advantage that it is not necessary to perform learning in the machine learning unit b. That is, the machine learning unit a has an advantage that the function obtained by the machine learning unit b by learning can be obtained by transmission of the weight B or the product obtained by processing the weight B so as to be applicable to the machine learning unit a without using the data used in the learning in the machine learning unit b. This is advantageous in that, in a case where the data used by the machine learning unit b for machine learning includes personal information such as medical information, the machine learning unit a can perform machine learning without transmission of the personal information from the machine learning unit b to the machine learning unit a.

It is noted that, in a case where there is a new machine learning unit c (not illustrated), the cooperative machine learning unit may transmit, to the machine learning unit c, the above-described weight B or a product obtained by processing the weight B so as to be applicable to the machine learning unit c. In this case, even in a case where the machine learning unit c does not perform the machine learning at all, there is an advantage that the machine learning unit c can realize a highly accurate function machine-learned in the machine learning unit a and the machine learning b without performing processing on the machine learning and without receiving personal information even in a case where the medical information includes the personal information.

In addition, an integrated machine learning unit may have a function of integrating weights acquired from the plurality of machine learning units and generating a weight usable in the plurality of machine learning units. A known technique may be used as a function itself of integrating respective weights and generating a weight.

In a case where the machine learning unit handles an image of bacteria, bacterial infection may have a regional characteristic. Therefore, for example, in the above-described example, considering a case in which the machine learning unit a is configured to process an image based on a specimen acquired from people in an area A, and the machine learning unit b is configured to process an image based on a specimen acquired from people in an area B different from the area A, a tendency of the image collected in the area A is different from a tendency of the image collected in the area B. Therefore, there is a possibility that a tendency of a content learned by the machine learning unit a and a tendency of a content learned by the machine learning unit b are different. Therefore, as described above, the integrated weight learned by the machine learning unit a is transmitted to the machine learning unit b, whereby the bacteria in the area A can be easily brought into the learned state also in the machine learning unit b. Therefore, for example, even in a case where the infection of the bacteria spreading in the area A starts to spread in the area B as well, or in a case where a person in the area B is infected by the bacteria in the area A by temporarily moving to the area A and returning to the area B to provide a specimen to the system of the present embodiment, there is an advantage of increasing a possibility that a determination can be made with higher accuracy in the area B with respect to the bacterial infection in the area A (even if the bacterial infection is rare in the area B). In addition, since the integrated weight learned by the machine learning unit b is transmitted to the machine learning unit a, there is an advantage that a situation opposite to the above-described situation can be realized. Furthermore, even in a case where there is the new machine learning unit c that processes an image based on a specimen acquired from people in the area C, it is also possible to increase an advantage that the machine learning unit c can learn about bacteria in the area A and/or the area B.

An example system including an integrated machine learning unit may include:

an acquisition unit configured to acquire a first weight generated by a first machine learning unit configured to perform machine learning of a relationship between a first image and appropriateness of the first image and/or a relationship between the first image and information specifying a first bacterial strain in the first image; and a transmission unit configured to transmit the first weight to a second machine learning unit different from the first machine learning unit.

Further, the example system including the integrated machine learning unit may be a system including:

an acquisition unit configured to acquires a first weight generated by a first machine learning unit configured to perform machine learning of a relationship between a first image and appropriateness of the first image and/or a relationship between the first image and information specifying a first bacterial strain in the first image;

an acquisition unit configured to acquires a second weight generated by a second machine learning unit configured to perform machine learning on a relationship between a second image and appropriateness of the second image and/or a relationship between the second image and information specifying a second bacterial strain in the second image; and a generation unit configured to integrate the first weight and the second weight and to generate a third weight usable by the first machine learning unit, the second machine learning unit different from the first machine learning unit, and/or a third machine learning unit different from the first and second machine learning units. Such a system may include a transmission unit configured to transmit the third weight to the first machine learning unit, the second machine learning unit, and/or the third machine learning unit.

2.5. Communication Unit

The communication unit has a communication function. The communication function may include a function of transmitting and/or receiving information. For example, the mobile terminal device according to the system of the present embodiment may transmit a captured image to be described later to the machine learning unit according to the system of the present embodiment. In addition, the mobile terminal device according to the system of the present embodiment may receive information specifying a corresponding bacterial strain and/or a certainty factor from the machine learning unit that has generated the information specifying the corresponding bacterial strain from the captured image and/or the certainty factor indicating a degree of correctness of inference by the machine learning unit. The information to be communicated is not limited thereto, and various types of information may be communicated.

2.6. Display Unit

The display unit has a display function. The display unit may be realized by a display device. The display device may be a display. Furthermore, the display device may also serve as an input device. For example, the display device may be a touch screen.

3. Embodiments

3.1. System According to First Embodiment

A system of the present embodiment has a function of supporting selection of an antimicrobial agent for a bacterial strain. A flow of processing of the system of the present embodiment will be described below with reference to FIG. 4.

Step 1.

The system of the present embodiment may acquire information specifying an antibiogram to be used (referred to as an "antibiogram to be used" in the document of the present application), and store the information therein.

The antibiogram indicates a relationship between a bacterial strain and an antimicrobial agent, and the relationship between the bacterial strain and the antimicrobial agent may include a sensitivity rate. The sensitivity rate for a specific bacterial strain and a specific antimicrobial agent indicates an effect when the specific antimicrobial agent is used for the specific bacterial strain, and the higher the sensitivity rate, the higher the effect of the antimicrobial agent.

In addition, the sensitivity rate of such an antibiogram may be associated with information indicating a specimen type. The information indicating the specimen type may include, for example, blood, urine, pus, and/or a virus.

The information specifying the antibiogram may be, for example, an antibiogram used by a facility to which a user belongs, an antibiogram provided by a prefecture, or other antibiograms. The antibiogram indicates an effect of an antimicrobial agent on bacteria, and such an effect may vary depending on various conditions. The various conditions may include, for example, geographical, natural, and biological differences. Since the system of the present embodiment can select an antibiogram to be used, there is an advantage of effectively using a case in which, for example, when the area A and the area B are different, antimicrobial agent β is more effective than antimicrobial agent α for a specific bacterial strain in the area A, but the antimicrobial agent α is more effective than the antimicrobial agent β for a specific bacterial strain in the area B. That is, there are various regional places where the system of the present embodiment is used, and as described above, there is an advantage of being able to use an appropriate antibiogram corresponding to a place in which the antibiogram is used by allowing the system of the present embodiment to select an antibiogram to be used.

By allowing a user to select one antibiogram to be used from among options of the plurality of antibiograms displayed by the system of the present embodiment, the system of the present embodiment may acquire information specifying the antibiogram to be used.

Figure 5:
FIG. 5 is a diagram illustrating a screen display example according to the system of the embodiment.

FIG. 5 is an example illustrating a situation in which the system of the present embodiment displays information specifying a plurality of antibiograms and receives selection from a user. This drawing is an example of a screen displayed such that an antibiogram of an own facility and an antibiogram of a prefecture can be selected.

A system according to another embodiment may store information specifying an antibiogram to be used in advance, and use an antibiogram to be used specified by the information specifying the antibiogram. In this case, step 1 may be omitted, and there is an advantage that convenience of a user may be improved.

In addition, the system according to another embodiment may download an antibiogram from a server, an information processing apparatus, and/or a cloud via the Internet. In addition, the system according to another embodiment may download an antibiogram as a selection candidate or an antibiogram to be used via the Internet according to a predetermined interval or update of the antibiogram. Here, the downloaded antibiogram may be an antibiogram corresponding to an area in which the system of the present embodiment is used. For example, the antibiogram may be set for each prefecture. In this case, as described above, there is an advantage of being able to use an antibiogram suitable for each area.

Step 2.

The system of the present embodiment may acquire information specifying a sensitivity rate serving as a threshold value (referred to as a "threshold sensitivity rate" in the document of the present application) and store the information therein. The threshold sensitivity rate may be, for example, a percentage such as 40%, 50%, 60%, 70%, and 80%, or a ratio. These may correspond to a method of describing a sensitivity rate indicated in an antibiogram.

The system of the present embodiment may display a plurality of sensitivity rates as candidates of the options, and the system of the present embodiment may acquire the threshold sensitivity rate by allowing a user to select one of the plurality of sensitivity rates.

The system of the present embodiment may display a plurality of sensitivity rates and may display information specifying a target bacterial strain. In this case, there is an advantage that a user can refer to the displayed sensitivity rates and information when selecting the sensitivity rate.

The system of the present embodiment may present information indicating a recommendation in association with one sensitivity rate out of the plurality of sensitivity rates. In this case, there is an advantage that a user can understand a recommended sensitivity rate among the plurality of sensitivity rate options without referring to other materials. The information indicating such a recommendation may be displayed in association with one sensitivity rate selected based on a specific criterion. The specific criterion may be, for example, a sensitivity rate generally recommended in relation to a bacterial strain. It is noted that even in a case where the information indicating such a recommendation is displayed, the system of the present embodiment may be configured to be able to select another sensitivity rate. In this case, there is an advantage that a user has a degree of freedom of being able to select a threshold sensitivity rate based on the past experience.

The system of another embodiment may previously store information specifying a sensitivity rate in association with information specifying a bacterial strain. In this case, the system of another embodiment may use the corresponding threshold sensitivity rate when using the information specifying the bacterial strain. In this case, step 2 may be omitted, and there is an advantage that convenience of a user may be improved.

Figure 6:
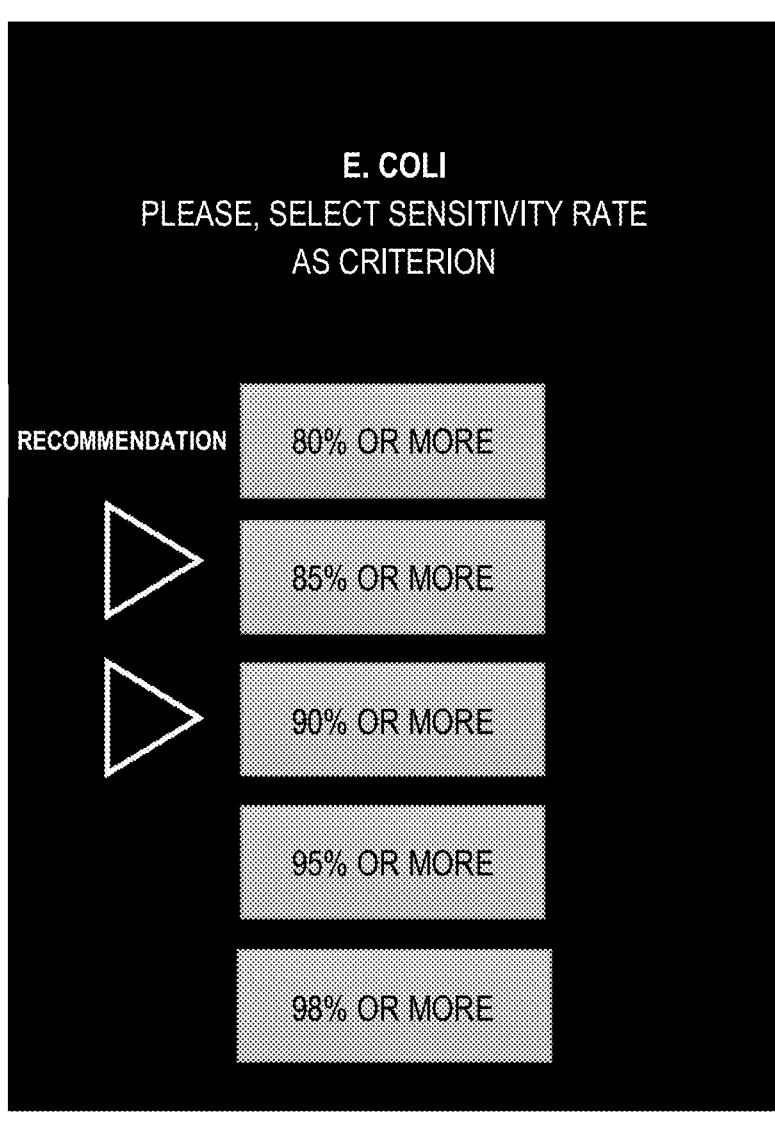
FIG. 6 is a diagram illustrating a screen display example according to the system of the embodiment.

FIG. 6 is an example illustrating a situation in which the system of the present embodiment displays a plurality of sensitivity rates and receives a selection from a user. In addition, this drawing is also an example of displaying a target bacterial strain together. In addition, this drawing is an example in which a sensitivity rate to be recommended is displayed in association with a sensitivity rate of 80%.

Step 3.

The system of the present embodiment acquires information specifying a target bacterial strain (referred to as "target bacterial strain information" in the document of the present application). The information specifying the bacterial strain may be a bacterial strain name or the like.

The system of the present embodiment may use target bacterial strain information generated by a machine learning unit in the system of the second embodiment to be described later, may use target bacterial strain information input by a user, or may use target bacterial strain information generated by another information processing apparatus accessible by the system of the present embodiment. In a case where the system of the present embodiment uses the target bacterial strain information generated by the machine learning unit in the system of the second embodiment to be described later, there is an advantage that the system of the present embodiment can be used seamlessly from a target image.

When the system according to the present invention is combined with the system according to the second embodiment to be described later, information specifying a bacterial strain generated by the system according to the second embodiment may be used. In this case, the system of the second embodiment may display both the information specifying the bacterial strain and information indicating a certainty factor of the information specifying the bacterial strain.

Figure 7:
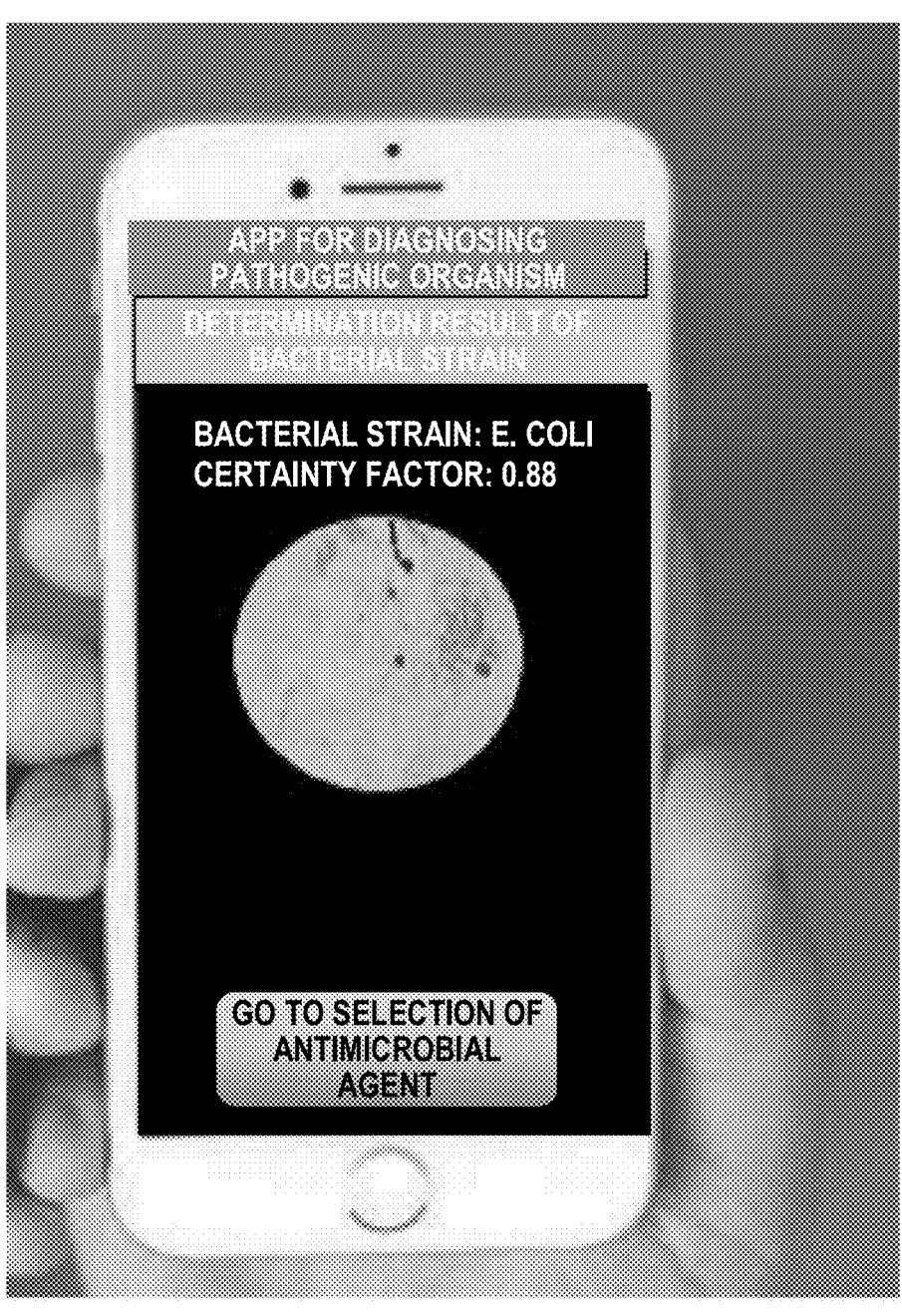
FIG. 7 is a diagram illustrating a screen display example according to the system of the embodiment.

For example, FIG. 7 illustrates "*E. coli*" as the information specifying the bacterial strain, and illustrates information indicating "0.88" as the information indicating the certainty factor.

In this case, there is an advantage that a user can understand with what degree of certainty factor the information specifying the bacterial strain generated by the system of the second embodiment has been generated by the system of the second embodiment. That is, in a case where a user considers that the information indicating the certainty factor is low, there is an advantage that the user can select other means to specify a bacterial strain.

It is noted that steps 1 to 3 may be processed in any order, or may be processed in an order different from the order described above.

Step 4.

The system of the present embodiment may specify, by using an antibiogram to be used and a threshold sensitivity rate, information on one or a plurality of antimicrobial agents, each sensitivity rate of which is equal to or higher than the threshold sensitivity rate, corresponding to target bacterial strain information.

The information on the antimicrobial agent may include information specifying an antimicrobial agent, and the information specifying the antimicrobial agent may include a name of the antimicrobial agent and/or an ID indicating the antimicrobial agent.

Here, the information on the antimicrobial agent may include a sensitivity rate of the antimicrobial agent, a spectrum score for the antimicrobial agent, AWaRe classification of the antimicrobial agent, and/or attention information on the antimicrobial agent. The system of the present embodiment may store, for each antimicrobial agent, the sensitivity rate of the antimicrobial agent, the spectrum score for the antimicrobial agent, the AWaRe classification of the antimicrobial agent, and/or the attention information on the antimicrobial agent in association with each other. Such associated data may be stored in a database accessible by the system of the present embodiment. For example, the system of the present embodiment may access a database by having the database including information on such an antimicrobial agent, or may access a database on another information processing apparatus on the Internet.

The sensitivity rate of the antimicrobial agent may be the sensitivity rate of the antimicrobial agent specified above with respect to the target bacterial strain information. The sensitivity rate is equal to or higher than the threshold sensitivity rate.

The spectrum score for the antimicrobial agent may include information indicating a wide and narrow range of effective bacterial strains. In order not to increase resistant bacteria, the spectrum score is preferably narrow (small).

The AWaRe classification of the antimicrobial agent may include, for example, Access that is considered to be usable, Watch that is considered to be used with caution because of resistance, Reserve that is considered to be used with care, and the like. The AWaRe classification may be defined by WHO.

The attention information on the antimicrobial agent may include information that a user pays attention when using the antimicrobial agent.

The attention information on the antimicrobial agent may include, for example, information on substitution for the spectrum score. Although the spectrum score is preferably presented for all antimicrobial agents, the spectrum score for all antimicrobial agents may not be provided or may not be prepared. When the system of the present embodiment cannot obtain information of a spectrum score for a specific antimicrobial agent, the system may acquire a spectrum score for another antimicrobial agent having a predetermined relationship with the specific antimicrobial agent and substitute the acquired spectrum score for the specific antimicrobial agent. In this case, the system of the present embodiment may include, as the attention information on the antimicrobial agent, the fact that a spectrum score for another antimicrobial agent is substituted for the spectrum score and/or such another antimicrobial agent.

In addition, the attention information on the antimicrobial agent may include, for example, information on a treatment to be recommended. The attention information on the antimicrobial agent may include, for example, the fact that a certain antimicrobial agent is recommended as an antimicrobial agent for a specific symptom, or the fact that a certain antimicrobial agent is not recommended as an antimicrobial agent for a specific symptom.

In addition, the attention information on the antimicrobial agent may include, for example, information on used sensitivity basis. The attention information on the antimicrobial agent may include, for example, information indicating "sensitivity of ESBL-producing bacteria is also determined based on a value of MIC".

It is noted that the system according to another embodiment may acquire information on a specimen type that is the basis of a bacterial strain in steps 1 to 3 described above. In this case, in step 4 described above, an antimicrobial agent corresponding to an input specimen type, the antimicrobial agent having sensitivity rate equal to or higher than a threshold sensitivity rate, may be specified. In this case, Step 5.

The system of the present embodiment may display information on one or a plurality of antimicrobial agents.

The system of the present embodiment may display information on one or a plurality of antimicrobial agents as information corresponding to target bacterial strain information, each of the antimicrobial agents having a sensitivity rate equal to or higher than a threshold sensitivity rate in an antibiogram to be used. That is, the system according to the present invention may display sensitivity rates of one or a plurality of the antimicrobial agents, spectrum scores for one or a plurality of the antimicrobial agents, AWaRe classification of one or a plurality of the antimicrobial agents, and/or attention information on one or a plurality of the antimicrobial agents.

For example, FIG. 8 shows an example in which the system of the present embodiment displays information on one or a plurality of antimicrobial agents as information corresponding to target bacterial strain information, each of the antimicrobial agents having a sensitivity rate equal to or higher than a threshold sensitivity rate in an antibiogram to be used.

In addition, the system of the present embodiment may display pieces of information on a plurality of antimicrobial agents in a specific order. In a case where pieces of information on a plurality of antimicrobial agents are specified, and there is a limitation on a display screen such as a mobile terminal device, there is an advantage that the pieces of information can be displayed in a meaningful order by a user.

For example, the system of the present embodiment may display pieces of information on antimicrobial agents in descending order of the sensitivity rate. In this case, there is an advantage that a user can know the pieces of information on the antimicrobial agents in descending order of the sensitivity rate.

In addition, as described above, the system of another embodiment may utilize an antibiogram including a sensitivity rate for each specimen type with respect to one antimicrobial agent. In this case, the system of the present embodiment may display a specimen type corresponding to the sensitivity rate as the information on the antimicrobial agent.

In a case where the system of the present embodiment is a mobile terminal device, there is an advantage that the system can be easily used in various places because the system is easy to move. For example, there is an advantage that a large amount of systems can be easily and quickly prepared even in a small medical institution, a medical site such as a disaster-stricken area that is not a medical institution, or the like. In addition, in a case where the system is used in a mobile terminal, there is an advantage that the system can be immediately used without special capital investment. In addition, in a case where a usage fee is set as the usage cost, for example, for each image used for inspection or for each usage time used for inspection, there is an advantage that an initial introduction cost is not required at the time of use, and the use can be started and stopped immediately.

3.2. System According to Second Embodiment

A system of the second embodiment has a function of generating information specifying a bacterial strain from an image. Hereinafter, processing of the system of the present embodiment will be described with reference to FIG. 9.

Before the system of the present embodiment captures an image of a specimen, such a specimen may be pretreated. For example, the specimen may be Gram stained. The specimen may include urine, blood, sputum, and/or cerebrospinal fluid. The image may be an image obtained by capturing an enlarged image of a Gram-stained specimen using a microscope.

Here, the specimen may be Gram stained by a simple staining kit. Such a staining kit may not be a part of the system of the present embodiment. Such a staining kit may include a specimen unit, a staining solution unit, and an observation unit. When the staining kit has a simple configuration of the specimen unit, the staining solution unit, and the observation unit, there is an advantage that a staining process can be easily handled at a usage site such as a disaster-stricken area or a medical underpopulated area.

The specimen unit and the observation unit may be connected by a flow path through which a specimen is movable. In addition, the staining solution unit and the observation unit may be connected by a flow path through which a staining solution is movable.

The specimen unit may hold urine, blood, sputum, or cerebrospinal fluid. These specimens may be several ml. In addition, the specimen may move from the specimen unit to the observation unit through a flow path by a predetermined method.

A chromosome unit may hold a staining solution. In addition, the staining solution may move from a staining unit to the observation unit through a flow path by a predetermined method. The predetermined method may be, for example, a method in which the staining solution moves to the observation unit by pressing down the staining solution. The staining solution may be Gram stain, acid-fast stain, or the like. In addition, a staining method may be performed by various methods, and for example, a Bartholomew & Mittwer method (Barmi method) using a reagent "Barmi M" manufactured by MUTO PURE CHEMICALS CO., LTD. may be used for the staining method. In addition, a reagent of the staining solution may be a Faber-G manufactured by NISSUI PHARMACEUTICAL CO., LTD.

The observation unit may include a place for observation. For example, the observation unit may be covered with transparent glass for ease of observation. In addition, the observation unit may be located at a place where a specimen moved from the specimen unit and a staining solution moved from the staining unit are mixed.

The following staining for the mode of use of the system of the present embodiment may be staining using the above-described staining kit or staining by other methods. Hereinafter, specific steps of the system of the present embodiment will be described.

Step 1

The system of the present embodiment acquires an image obtained by capturing an image of a pretreated specimen (the image may be referred to as a "captured image" in the document of the present application).

The captured image may be captured by an imaging function of the system of the present embodiment, or may be captured by another imaging device. In the latter case, the system of the present embodiment may acquire an image captured by another imaging device.

Step 2

The system of the present embodiment may perform pre-processing on the captured image.

The pre-processing may include processing of confirming appropriateness of the image. The processing of confirming the appropriateness of the image may include processing of confirming appropriateness of a position of the image, and may include, for example, processing of confirming whether a portion in an image obtained by imaging a specimen is a portion suitable for application of machine learning for inferring a bacterial strain to be described later. Furthermore, the processing of confirming the appropriateness of the image may include, for example, processing of confirming appropriateness of an image itself, and may include, for example, processing of confirming whether a captured image is in focus with a specimen.

Such pre-processing may be processed by a machine learning inference function of a machine learning unit included in the system of the present embodiment. For example, the machine learning unit of the system of the present embodiment may have machine-learned a relationship between an image and appropriateness of a position of the image, and output the appropriateness of the position of the image with respect to a captured image. The appropriateness of the position of the image may be any one of two types of information, that is, the position is appropriate and the position is not appropriate, or may be information indicating a direction in which the position of the image is to be moved. In addition, for example, the machine learning unit of the system of the present embodiment may have machine-learned a relationship between an image and consistency of focus of a specimen, and output the consistency of focus of the specimen with respect to a captured image. The consistency of focus of the specimen may be any one of two types of information, that is, the focus is out of a predetermined allowable range and the focus is within a predetermined allowable range, or may be information indicating an allowable degree of focus.

When the system according to the present invention performs pre-processing on an image, an alert may be presented in a case where the image is an inappropriate image. The alert may include presentation of inappropriateness of a position and/or presentation of consistency of focus of an image depending on a content of confirmation of the pre-processing. The alert may include a voice and/or a display on a display unit. The alert may include an indication, to a user, that an image is not appropriate. The alert may also include a content that explains, to a user, why an image is inappropriate. Furthermore, the alert may include a content that explains, to a user, what action should be taken. In response to such an alert, a user can artificially change an image or the like and proceed to the step of generating information specifying a bacterial strain for an image, which will be described later, with respect to an appropriate image. Therefore, there is an advantage that accuracy of generating the information specifying a bacterial strain can be improved.

Step 3

The system of the present embodiment may infer the information specifying a bacterial strain corresponding to a captured image using a machine learning unit that has machine-learned a relationship between an image and the information specifying the bacterial strain.

The machine learning unit according to the system of the present embodiment may have machine-learned the relationship between the image and the information specifying the bacterial strain. The relationship between the image and the information specifying the bacterial strain given as teaching data may be used. The machine learning unit according to the system according to the present invention may generate, using such a relationship, information specifying a bacterial strain for the bacterial strain captured in a captured image with respect to the captured image.

In a case where the system according to the present invention uses the machine learning function, there is an advantage that information specifying a bacterial strain can be easily generated.

FIG. 10 schematically illustrates a function of the machine learning unit. It is noted that, although both at the time of learning and at the time of inference are described in the present drawing, as described above, the learning unit according to the system according to the present invention may include both functions or may have an inference function without including a learning function.

Step 4

The system of the present embodiment may display an inference result regarding information on a bacterial strain The information on the bacterial strain may include information specifying a bacterial strain. In addition, the information on the bacterial strain may include a certainty factor regarding the information specifying the bacterial strain and/or information used at the time of inference.

The system of the present embodiment may display the information specifying a bacterial strain, the certainty factor regarding the information specifying the bacterial strain, and/or the information used at the time of inference. For example, the system according to the present invention may display a captured image and display, on the captured image, a feature amount used at the time of inference by the machine learning unit in association with the captured image. In this case, there is an advantage that a user can understand which feature amount in the image is used as a reference to perform inference.

For example, FIG. 11 is an example of displaying information used by the machine learning unit at the time of inference. In this drawing, a portion such as an island is a portion regarded as important at the time of inference, and the rest of portions are portions not regarded as important. As described above, the system according to the present embodiment may display a portion weighted, using the machine learning unit, by a predetermined value or more at the time of inference and a portion weighted, using the machine learning unit, by a value less than the predetermined value in a distinguished manner. The distinguishing mode may be, for example, a color or a form in the figure.

In the usage example of the system to be described later, culture inspection is performed on a bacterial strain estimated in 4, and a laboratory technician or a doctor confirms the bacterial strain in about one day to five days. The system of the present embodiment may acquire and store such confirmed bacterial strain. For example, the system of the present embodiment may store information on the confirmed bacterial strain and the above-described captured image of the confirmed bacterial strain in association with each other. In addition, the machine learning unit in the system of the present embodiment may perform machine learning on a relationship between the above-described captured image of the confirmed bacterial strain and the information on the confirmed bacterial strain. With such machine learning, there is an advantage that it is possible to perform machine learning on a relationship between information on a bacterial strain considered to be correct by actual culture and an image, and to further improve accuracy of estimation by machine learning. Furthermore, these pieces of machine-learned information may be used in the above-described cooperative machine learning unit.

3.3. Usage Example of Systems of First and Second Embodiments

Next, an example of use of the systems of the first and second embodiments will be described.

Conventionally, the following steps are taken to determine a treatment policy for prescribing an antimicrobial agent based on a patient's specimen.

1. First, a specimen of a target patient is Gram stained to generate a preparation.

2. Next, bacterial strain estimation is performed by a technician, a doctor, or the like using an optical microscope. Here, experience of a technician, a doctor, or the like is required, and as the required time, time of 2 to 3 minutes is required per case.

3. An initial treatment policy is determined based on the above bacterial strain estimation. The determination of such a treatment policy is based on empirical evidence.

4. Culture inspection is performed on the estimated bacterial strain, and a laboratory technician or a doctor confirms the bacterial strain.

5. The result of a chemical agent sensitivity test is checked.

6. The treatment policy of antimicrobial agent prescription is determined.

The system according to the second embodiment and the system according to the first embodiment described above are systems that replace the step of estimating bacterial strains of 2 among the above-described steps. For example, as described above, the system of the second embodiment or another system specifies information specifying a bacterial strain, and the system of the first embodiment specifies information on an antimicrobial agent.

When the system of the present embodiment is used in the above-described flow, there is an advantage that it is possible to support the experience of a technician or a doctor in the bacterial strain estimation in the above-described step 2. Particularly, there is an advantage that it is possible to support determination of an initial treatment policy by a doctor based on objective information in a medical site requiring a quick response in a situation where there is a shortage of personnel, such as a disaster-stricken area.

In addition, in a case where the system of the second embodiment displays a feature amount of an image particularly at the time of inferring a bacterial strain, since a doctor who determines a treatment policy can understand the feature amount of the image used as the basis of the bacterial strain inference, that is, what viewpoint in the image is focused on to specify information specifying the bacterial strain, there is an advantage that a doctor himself or herself can easily determine a treatment policy while comparing the treatment policy with his or her own sense as compared with a case in which only conclusion such as a bacterial strain name is displayed.

3.4. Third Embodiment

A system according to a third embodiment is an application example with respect to a virus. For example, in the system of the present embodiment, a machine learning unit that has machine-learned a relationship between an image obtained by capturing a virus and information specifying the virus may generate information specifying a corresponding virus with respect to a captured image of the virus captured by an electron microscope. In addition, the system of the present embodiment may be capable of specifying a corresponding antiviral agent based on the information specifying the virus. In this case, the system of the present embodiment may specify the antiviral agent using a rule that defines a relationship between a virus and the antiviral agent.

3.5. Regarding Various Embodiments

A mobile terminal device according to a first aspect includes:

"an acquisition unit configured to acquire information specifying a bacterial strain and information specifying a sensitivity rate; and a specification unit configured to specify, using an antibiogram, information on one or a plurality of antimicrobial agents, each of the antimicrobial agents satisfying the sensitivity rate for the bacterial strain".

A mobile terminal device according to a second aspect is a mobile terminal device, in which "the information on the antimicrobial agent includes a sensitivity rate of the antimicrobial agent, a spectrum score for the antimicrobial agent, and/or an AWaRe classification of the antimicrobial agent" in the first aspect.

A mobile terminal device according to a third aspect is a mobile terminal device, in which "the mobile terminal device includes a display unit configured to display a plurality of sensitivity rate candidates; and the sensitivity rate is selected, by a user, from among the plurality of sensitivity rate candidates" in the first or second aspect.

A mobile terminal device according to a fourth aspect is a mobile terminal device, in which "the display unit displays information indicating a recommendation in association with one of the plurality of sensitivity rate candidates" in any one of the first to third aspects.

A mobile terminal device according to a fifth aspect is a mobile terminal device, in which "the display unit displays a plurality of available candidates for the antibiogram, and the antibiogram is an antibiogram selected by the user" in any one of the first to fourth aspects.

A mobile terminal device according to a sixth aspect further includes:

"an image acquisition unit configured to acquire a first image;

a transmission unit configured to transmit the first image; and a reception unit configured to receive the information specifying the bacterial strain, in which the information specifying the bacterial strain is generated by allowing a machine learning unit to apply the first image, the machine learning unit being not provided in the mobile terminal device and completing machine learning of a relationship between an image and the information specifying the bacterial strain" in any one of the first to fifth aspects.

A mobile terminal device according to a seventh aspect further includes "a display unit configured to display the information specifying the bacterial strain, the information being generated by allowing the machine learning unit to apply the first image, and a certainty factor indicating a degree of correctness of inference by the machine learning unit" in any one of the first to sixth aspects.

A mobile terminal device according to an eighth aspect is a mobile terminal device, in which "the display unit further displays a feature amount in association with the first image, the feature amount being used when the machine learning unit performs the inference" in any one of the first to seventh aspects.

A mobile terminal device according to a ninth aspect is a mobile terminal device, in which "the image acquisition unit detects appropriateness of the acquired image, and generates an alert upon determining that the acquired image is inappropriate" in any one of the first to eighth aspects.

A mobile terminal device according to a tenth aspect is a mobile terminal device, in which "the bacterial strain relates to urine, blood, sputum, and/or cerebrospinal fluid" in any one of the first to ninth aspects.

A mobile terminal device according to an eleventh aspect is a mobile terminal device, in which "the information specifying the bacterial strain is specified by a method other than the machine learning" in any one of the first to tenth aspects.

A mobile terminal device according to a twelfth aspect is a mobile terminal device, in which "the information on the antimicrobial agent includes attention information on the antimicrobial agent" in any one of the first to eleventh aspects.

A method according to a thirteenth aspect "includes, by a mobile terminal device, steps of:

acquiring information specifying a bacterial strain and information specifying a sensitivity rate; and specifying, using an antibiogram, information on one or a plurality of antimicrobial agents, each of the antimicrobial agents satisfying the sensitivity rate for the bacterial strain".

A method according to a fourteenth aspect is a method, in which "the mobile terminal device includes a memory that stores the antibiogram" in the thirteenth aspect.

A method according to a fifteenth aspect is a method, in which "the mobile terminal device includes a calculation device that processes calculation to specify information on the antimicrobial agent" in the thirteenth of fourteenth aspect.

A program according to a sixteenth aspect "causes a mobile terminal device to operate as:

a unit configured to acquire information specifying a bacterial strain and information specifying a sensitivity rate; and a unit configured to specify, using an antibiogram, information on one or a plurality of antimicrobial agents, each of the antimicrobial agents satisfying the sensitivity rate for the bacterial strain".

A program according to a seventeenth aspect is a program, in which "the mobile terminal device includes a memory that stores the antibiogram" in the sixteenth aspect.

A program according to an eighteenth aspect is a program, in which "the mobile terminal device includes a calculation device that processes calculation to specify the information on the antimicrobial agent" in the sixteenth or seventeenth aspect.

A system according to a nineteenth aspect includes:

"a reception unit configured to receive a first image;

the machine learning unit configured to complete machine learning of a relationship between an image and information specifying a bacterial strain; and a transmission unit configured to receive the information specifying the bacterial strain, in which the information specifying the bacterial strain is generated by allowing the machine learning unit to apply the first image".

Although configurations implemented by the system of the present example have been described above, these configurations may be configurations implemented by one or a plurality of information processing apparatuses in the system.

In addition, the system according to the present invention may not have a function of performing management such as acquisition, storage, and/or distinguishment of personal information such as patient privacy. For example, the system according to the present invention may not have a function of storing information specifying a patient and a captured image in association with each other, a function of storing the information specifying the patient and information specifying a bacterial strain related to a specimen in association with each other, a function of storing the information specifying the patient and information on an antimicrobial agent used by the patient in association with each other, and the like. Since the system according to the present invention does not have a function of managing personal information of a patient as described above, there is an advantage that the system can be used without being restricted by the Personal Information Protection Act or the like. In recent years, the interest in privacy has increased, and the protection by the Personal Information Protection Act has been strengthened. Therefore, the system according to the present invention has a high advantage in terms of not using personal information.

Furthermore, the system according to the present invention may have a function of performing management such as acquisition, storage, and/or distinguishment of anonymized information of a patient, in addition to or instead of the above described function. Since the system according to the present invention has a function of managing anonymized information of a patient, there is an advantage that the system can be used without restriction on personal information, such as transfer to a third party, unlike personal information.

In addition, the system according to the present invention is not intended to perform definite diagnosis of bacterial infection on behalf of a doctor, and may assist a doctor in estimating a bacterial strain. In this case, the system according to the present invention is not a medical device, and has an advantage that the system is not subject to various restrictions as a medical device.

In the system according to the document of the present application, urine, blood, sputum, and/or cerebrospinal fluid for animals such as livestock, poultry, and/or wild animals may be used in addition to or instead of humans. Particularly, in recent years, the number of zoonotic diseases has increased, and conservation of an ecosystem on the earth can be achieved for the first time by both human and animal health, and in order to realize and maintain the conservation, efforts for maintaining the health of humans and animals are required.

In the document of the present application, the system may include a mobile terminal device. The mobile terminal device may include a smartphone, a mobile phone, a PDA, a wearable computer, a tablet computer, a handheld computer, a notebook computer, or a laptop.

In the system according to the document of the present application, a mode of displaying information to a user has been mainly described as a mode of transmitting information to a user. However, a mode in which a user is notified by voice may be used in addition to or instead of such a display mode.

It goes without saying that the invention examples described in the embodiments of the document of the present application are not limited to those described in the document of the present application, and can be applied to various examples within the scope of the technical idea.

In addition, the processing and procedures described in the document of the present application may be realized not only by those explicitly described in the embodiments but also by software, hardware, or a combination thereof. In addition, the processing and procedures described in the document of the present application may be implemented as a computer program and executed by various computers. Furthermore, the computer program may be capable of being recorded in a non-transitory recording medium. The recording medium may be a computer-readable recording medium.

The invention claimed is:

1. A mobile terminal device comprising a processor and memory, the memory storing computer-readable instructions that when executed cause the processor to:

acquire information specifying a bacterial strain and information specifying a sensitivity rate; and specify, using an antibiogram, information on one or a plurality of antimicrobial agents, each of the antimicrobial agents satisfying the sensitivity rate for the bacterial strain, wherein the mobile terminal device includes a display device configured to display a plurality of sensitivity rate candidates, and the sensitivity rate is selected, by a user, from among the plurality of sensitivity rate candidates.

2. The mobile terminal device according to claim 1, wherein the information on the antimicrobial agent includes a sensitivity rate of the antimicrobial agent, a spectrum score for the antimicrobial agent, and/or an AWaRe classification of the antimicrobial agent.

3. The mobile terminal device according to claim 1, wherein the display device displays information indicating a recommendation in association with one of the plurality of sensitivity rate candidates.

4. The mobile terminal device according to claim 3, wherein the display device displays a plurality of available candidates for the antibiogram, and the antibiogram is an antibiogram selected by the user.

5. The mobile terminal device according to claim 1, further comprising:

an image acquisition device configured to acquire a first image;

a transmission device configured to transmit the first image; and a reception device configured to receive the information specifying the bacterial strain, wherein the information specifying the bacterial strain is generated by allowing a machine learning unit to apply the first image, the machine learning unit being not provided in the mobile terminal device and completing machine learning of a relationship between an image and the information specifying the bacterial strain.

6. The mobile terminal device according to claim 5, further comprising a display device configured to display the information specifying the bacterial strain, the information being generated by allowing the machine learning unit to apply the first image, and a certainty factor indicating a degree of correctness of inference by the machine learning unit.

7. The mobile terminal device according to claim 6, wherein the display device further displays a feature amount in association with the first image, the feature amount being used when the machine learning unit performs the inference.

8. The mobile terminal device according to claim 5, wherein the image acquisition device detects appropriateness of the acquired image, and generates an alert upon determining that the acquired image is inappropriate.

9. The mobile terminal device according to claim 1, wherein the bacterial strain is related to urine, blood, sputum, and/or cerebrospinal fluid.

10. The mobile terminal device according to claim 1, wherein the information specifying the bacterial strain is specified by a method other than machine learning.

11. The mobile terminal device according to claim 1, wherein the information on the antimicrobial agent includes attention information on the antimicrobial agent.

12. A computer-implemented method comprising by a processor in a mobile terminal device:

acquiring information specifying a bacterial strain and information specifying a sensitivity rate; and calculating, using an antibiogram, information on one or a plurality of antimicrobial agents, each of the antimicrobial agents satisfying the sensitivity rate for the bacterial strain, wherein the mobile terminal device includes a display device configured to display a plurality of sensitivity rate candidates, and the sensitivity rate is selected, by a user, from among the plurality of sensitivity rate candidates.

13. The computer-implemented method according to claim 12, wherein the mobile terminal device includes a memory that stores the antibiogram.

14. The computer-implemented method according to claim 12, wherein the mobile terminal device includes a calculation device that processes calculation to specify the information on the antimicrobial agent.

15. Non-transitory computer readable storage media storing computer-readable instructions, which when executed by a processor in a mobile terminal device, cause the processor to:

acquire information specifying a bacterial strain and information specifying a sensitivity rate; and calculate to specify, using an antibiogram, information on one or a plurality of antimicrobial agents, each of the antimicrobial agents satisfying the sensitivity rate for the bacterial strain, wherein the mobile terminal device includes a display device configured to display a plurality of sensitivity rate candidates, and the sensitivity rate is selected, by a user, from among the plurality of sensitivity rate candidates.

16. The non-transitory computer readable storage media according to claim 15, wherein the mobile terminal device includes a memory that stores the antibiogram.

17. The non-transitory computer readable storage media according to claim 15, wherein the mobile terminal device includes a calculation device that processes calculation to specify the information on the antimicrobial agent.

* * * * *